United States Patent
Rogers et al.

(10) Patent No.: US 6,186,785 B1
(45) Date of Patent: Feb. 13, 2001

(54) TORQUE INDICATOR RATCHET WRENCH FOR DENTISTRY

(75) Inventors: Dan Paul Rogers, Royal Palm Beach; Thomas Tait Robb, Stuart, both of FL (US)

(73) Assignee: Implant Innovations, Inc., Palm Beach Gardens, FL (US)

( * ) Notice: Under 35 U.S.C. 154(b), the term of this patent shall be extended for 0 days.

(21) Appl. No.: 09/470,555

(22) Filed: Dec. 22, 1999

Related U.S. Application Data

(60) Provisional application No. 60/113,463, filed on Dec. 23, 1998, and provisional application No. 60/136,516, filed on May 28, 1999.

(51) Int. Cl.⁷ ..................................................... A61C 8/00
(52) U.S. Cl. ............................ 433/141; 433/173; 81/471
(58) Field of Search ..................................... 433/141, 163, 433/173, 174; 81/483, 48, 471

(56) References Cited

U.S. PATENT DOCUMENTS

| | | |
|---|---|---|
| 2,151,953 | 3/1939 | Zimmerman . |
| 4,129,035 * | 12/1978 | Ango ........................................ 73/139 |
| 5,129,293 * | 7/1992 | Larson et al. ........................... 81/483 |
| 5,366,412 | 11/1994 | Beaty et al. ............................. 464/38 |
| 5,368,480 | 11/1994 | Balfour et al. ......................... 433/141 |
| 5,397,269 | 3/1995 | Beaty et al. ............................. 464/38 |
| 5,433,665 | 7/1995 | Beaty et al. ............................. 464/38 |
| 5,437,550 | 8/1995 | Beaty et al. ........................... 433/141 |
| 5,725,376 | 3/1998 | Poirier ................................... 433/172 |
| 5,734,113 | 3/1998 | Vogt et al. ........................ 73/862.23 |

FOREIGN PATENT DOCUMENTS

| | | |
|---|---|---|
| 92 08 014 | 7/1992 | (DE) . |
| 42 00 364 | 9/1993 | (DE) . |
| 195 07 535 | 9/1996 | (DE) . |
| 0 428 490 | 5/1991 | (EP) ................................ A61C/8/00 |
| 0 704 281 | 4/1996 | (EP) . |
| WO97/47436 | 12/1997 | (WO) ............................... B25B/23/00 |
| WO98/55039 | 12/1998 | (WO) ................................ A61C/8/00 |

OTHER PUBLICATIONS

Carlsson et al., "Removal Torqus for Polished and Rough Titanium Implants," *The Int'l Journal of Oral & Maxillofacial Implants*, vol. 3, No. 1, (1988, pp. 21–24.

"3i Surgica Catalog", Implant Innovations Inc., Jul. 1997, Cover Page and pp. 54–60.

* cited by examiner

*Primary Examiner*—Nicholas D. Lucchesi
(74) *Attorney, Agent, or Firm*—Jenkens & Gilchrist

(57) ABSTRACT

This present invention relates to a ratchet wrench and a torque indicator combined concentrically in a single housing. The ratchet wrench is useful for driving a fastener used in dentistry, such as an abutment screw that holds an abutment on a dental implant. In operation, the handle of the wrench can be rotated in one direction (e.g. clockwise) to impart torque on the fastener. When the handle is rotated in the opposite direction (e.g. counterclockwise), no torque is applied to the fastener as the handle is returned to a position where it is easy for the clinician to again rotate the handle to apply additional torque to the fastener. The return motion of the handle (e.g. counterclockwise rotation) may be stepless in operation which is brought about through a coiled clutch spring located in an annular space within a housing between the housing and a concentric driver member. To provide an indication of torque, a rotor body is supported coaxially within the driver member. Torque indicator marks on the rotor body and the driver member indicate angular displacement of the driver member around the common axis relative to the rotor body when a tool held in the rotor body is restrained from turning under load. The housing and with it the drive member may be turned by hand around their common axis when the housing is turned in the latched direction, or a handle fixed to the housing may be used. A lubricating washer is supplied to reduce friction within the ratchet wrench.

41 Claims, 12 Drawing Sheets

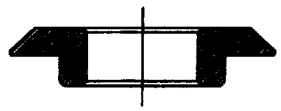
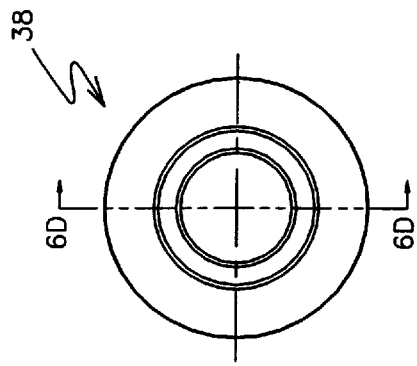
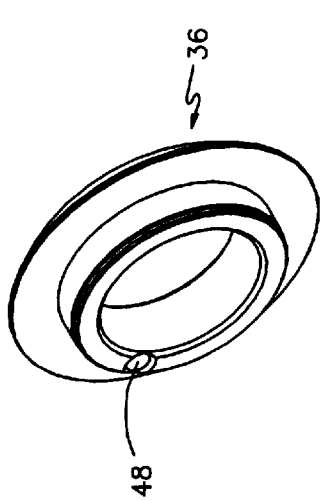
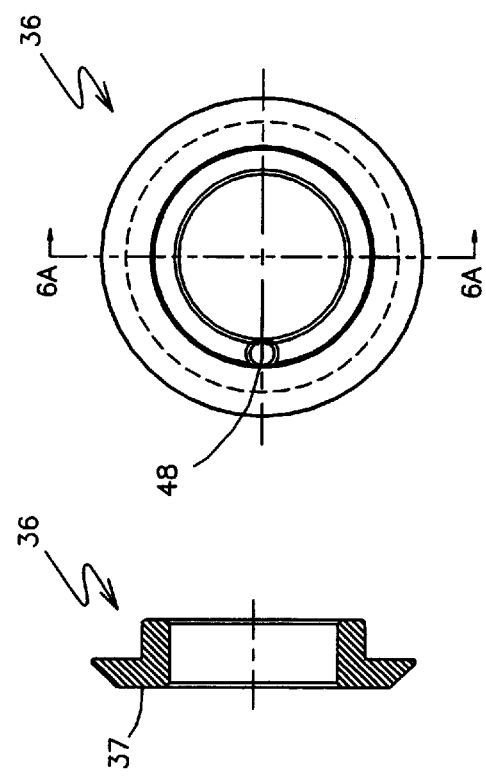
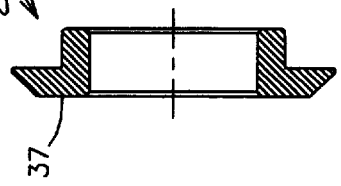

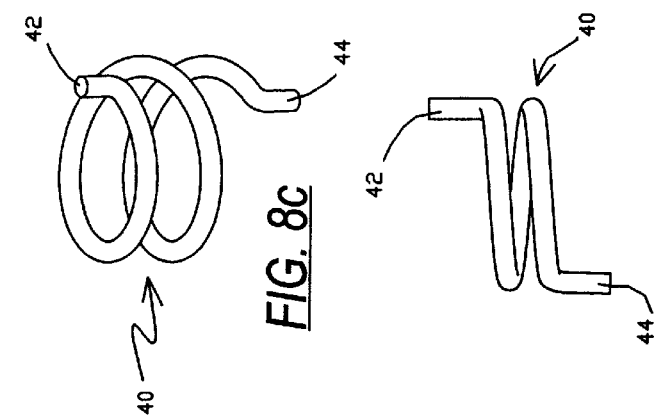
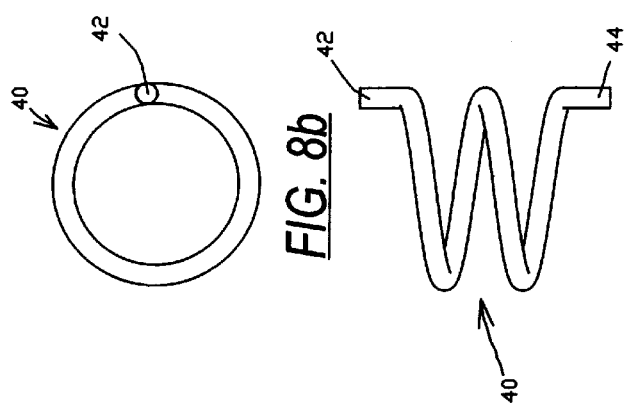
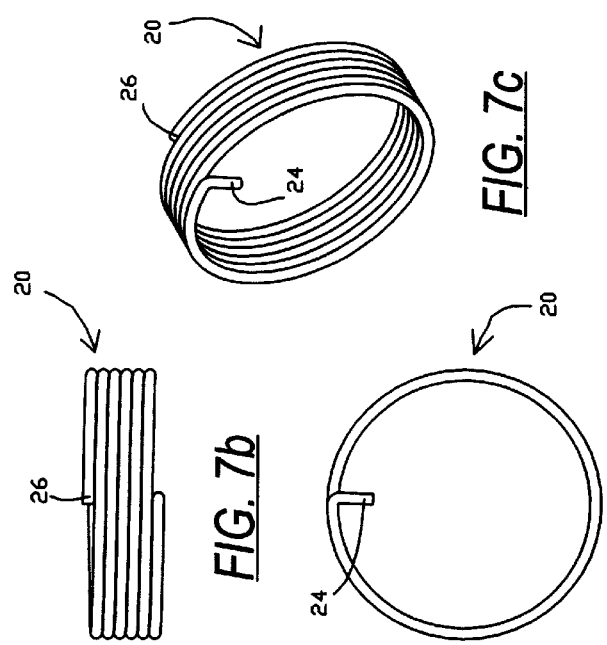

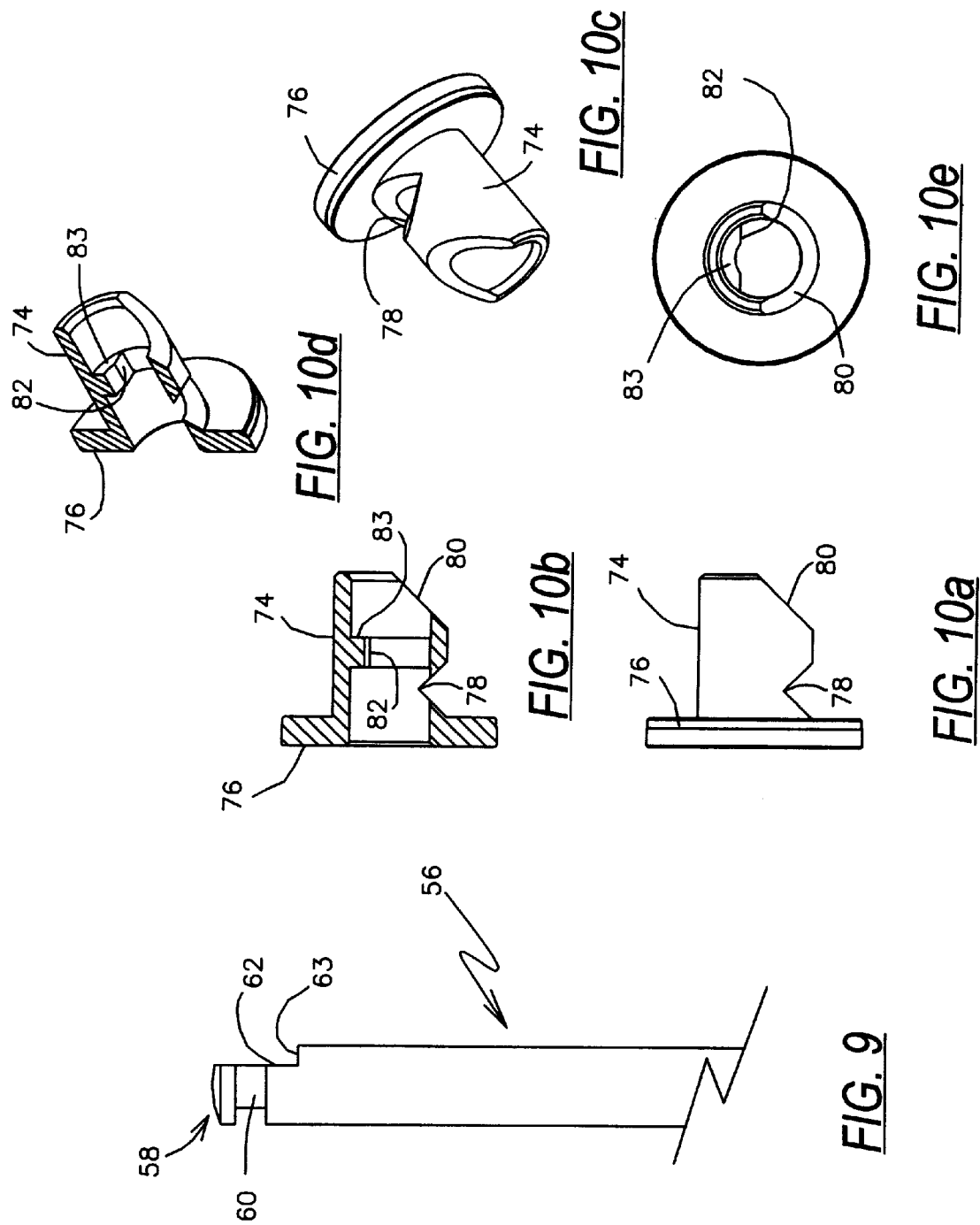

TORQUE INDICATOR RATCHET WRENCH FOR DENTISTRY

CROSS-REFERENCE TO RELATED APPLICATIONS

This is a complete application claiming the benefit of Provisional Application Ser. No. 60/113,463, filed Dec. 23, 1998, and Ser. No. 60/136,516, filed May 28, 1999.

FIELD OF THE INVENTION

This present invention relates to a ratchet wrench that includes a torque indicator that progressively indicates the amount of torque that is be exerted on the screw or bolt each time the wrench is rotated and then ratcheted back to its starting position. In particular, the present invention relates to dental ratchet wrench with torque indication for dentistry.

BACKGROUND OF THE INVENTION

While ratchet wrenches have been used in the previously used in various fields including dentistry, it is particularly useful to know the amount of torque that each partial rotation and subsequent ratcheting of the wrench places on the screw or bolt. Thus, unlike a torque limiter, which does not allow the torque to exceed a certain amount, a need exists for a ratchet wrench having a torque indicator that progressively indicates the torque as it is being exerted on the bolt or screw. Further, a need exists for this device to be located in a relatively small housing especially when it is to be used in small regions, such as in the mouth.

SUMMARY OF THE INVENTION

This specification describes a ratchet wrench and a torque indicator combined concentrically in a single housing. The ratchet wrench is useful for driving a fastener used in dentistry, such as an abutment screw which holds an abutment on a dental implant. In operation, the handle of the wrench can be rotated in one direction (e.g. clockwise) to impart torque on the fastener. When the handle is rotated in the opposite direction (e.g. counterclockwise), no torque is applied to the fastener as the handle is returned to a position where it is easy for the clinician to again rotate the handle to apply additional torque to the fastener.

The return motion of the handle (e.g. counterclockwise rotation) may be stepless in operation which is brought about through a coiled clutch spring located in an annular space within a housing between the housing and a concentric driver member. The clutch spring has one end fixed to one of the housing and the driver member and the other end free in the annular space between them. Preferably, the part of the annular space containing the free end is thinner than the part of the annular space containing the fixed end of the clutch spring. Depending on the direction in which the clutch spring is coiled, its free end will slip in the annular space when relative rotation around is imparted in one direction between the housing and the driver member. However, it will latch the housing and the driver member against relative rotation in the opposite direction. Alternatively, the return motion of the wrench can be accomplished by using an overrunning or detent clutch which provides a "click"-type action.

To provide an indication of torque, a rotor body is supported coaxially within the driver member. A torsion spring located between the rotor body and driving member is fixed at one end to the rotor body and at its other end to the driving member. This rotor body is adapted to hold one or more wrench tools in one or more sockets located on the common axis. Torque indicator marks on the rotor body and the driver member indicate angular displacement of the driver member around the common axis relative to the rotor body when a tool held in the rotor body is restrained from turning under load. The housing and with it the drive member may be turned by hand around their common axis when the housing is turned in the latched direction. Or, a handle fixed to the housing may be used to turn the housing around the common axis. The torque indicator marks indicate torque at the axis of rotation of a tool. The fixed handle does not participate in this measurement, and can therefore be of a simple, stiff design. The rotor body may be provided with a receptor for an ISO-type dental latch, as well as a socket or receptor for another type of tool.

BRIEF DESCRIPTION OF THE DRAWINGS

FIGS. 6a, 6b and 6c are cross-sectional, end and isometric views, respectively, of the rotor housing hub of FIG. 1;

FIGS. 6d, 6e and 6f are cross-sectional, end and isometric views, respectively, of the rotor body hub of FIG. 1;

FIGS. 7a, 7b and 7c are side, end and isometric views, respectively, of the clutch spring of FIG. 1;

FIGS. 8a, 8b and 8c are side, end and isometric views, respectively, of the torsion spring of FIG. 1;

FIG. 8d shows another embodiment of the torsion spring;

FIG. 9 illustrates an "ISO" type dental latch used to connect dental tools in dental handpieces;

FIGS. 10a–e are various views, respectively, of the ISO-type latch body;

FIGS. 12a–12j, inclusive, are a sequence of figures showing the steps of installing and removing a tool having an ISO-type latch into and from a holder for such tools;

DETAILED DESCRIPTION OF THE DRAWINGS

Figure 2:
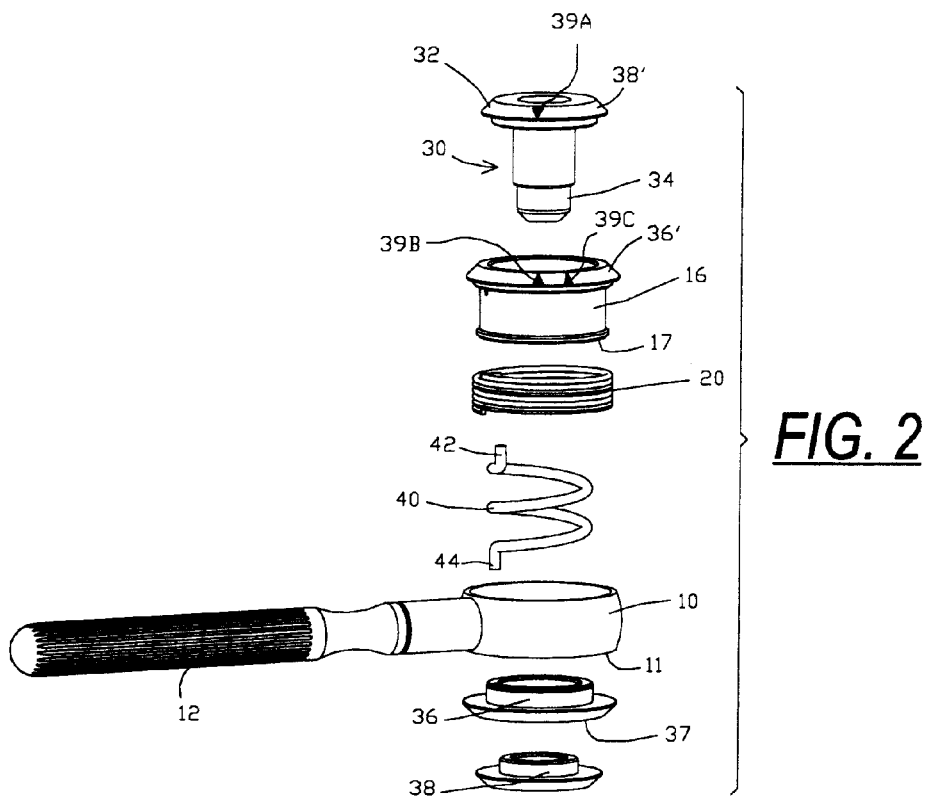
FIG. 2 is an exploded view of FIG. 1.
Figure 1:
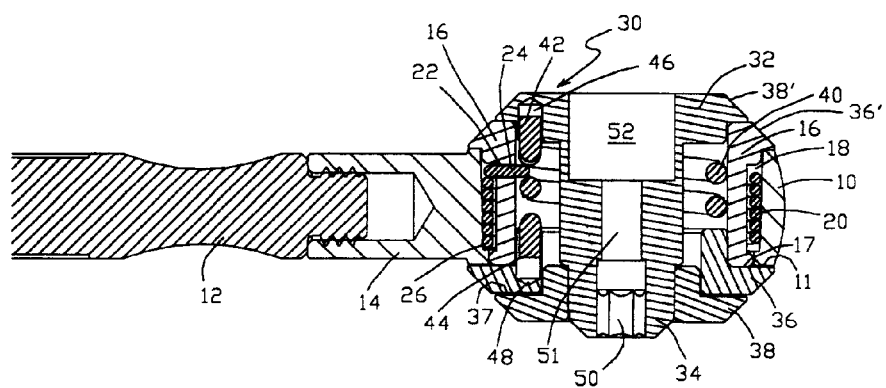
FIG. 1 is a longitudinal sectional view of the wrench.
Figure 3:
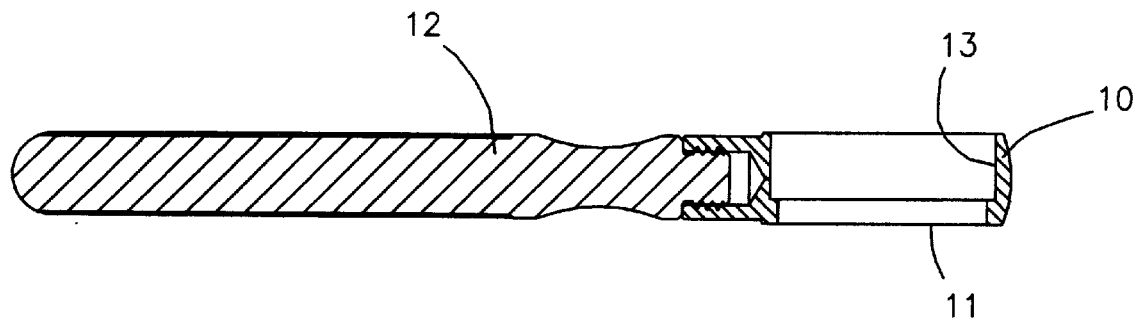
FIG. 3 is a longitudinal sectional view of the housing and handle of FIG. 1.
Figure 4A:
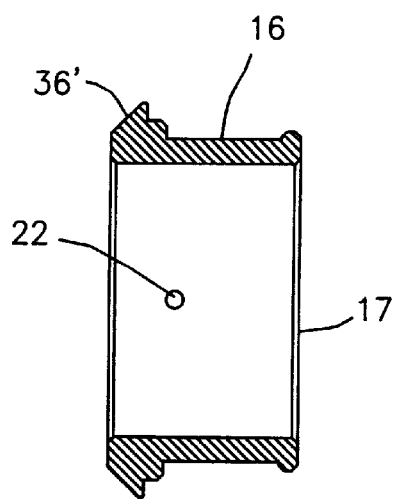
FIGS. 4a and 4b are cross-sectional and end views, respectively, of the driver member of FIG. 1.
Figure 4B:
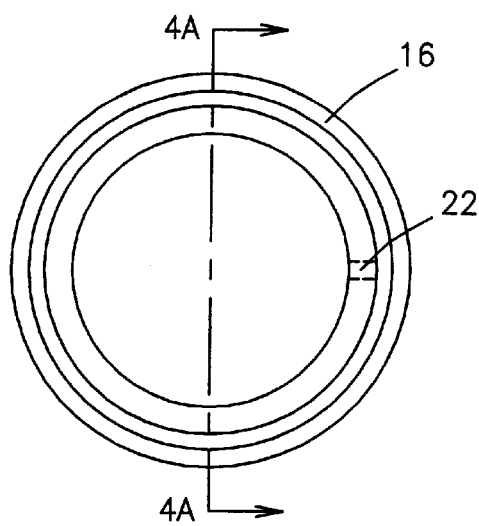

Referring now to FIGS. 1, 2 and 3, the housing 10 has a handle 12 attached to a boss 14 at one side of the housing 10. A drive member 16 is concentrically located within the housing 10 and, together with the housing, defines an annular space 18 containing the coiled clutch spring 20. The drive member 16 and the clutch spring 20 are shown in greater detail in FIGS. 4 and 7, respectively.

The drive member 16 has a hole 22 in its side wall above its lower end 17. (See FIG. 4.) The clutch spring 20 has a series of coils and is bent radially inward at one end 24 with its other end 26 being open, or "free". (See FIG. 7.) The coiled clutch spring 20 is located in the annular space 18 with its bent end 24 passing through the hole 22 in the side wall of the drive member 16. The open end 26 of the clutch spring 20 rests in the bottom region of the annular space 18 as seen in FIG. 1.

Preferably, the annular space 18 is made narrower at its bottom region near the open end 26 than at its top region near its bent end 24 (as seen in FIG. 1). To provide this variation in the annular space 18, an inner wall 13 of the housing 10 is curved on a smaller radius near the bottom end 11 than at the opposite or top end. The narrower portion of the annular space 18 serves to confine the open end 26 against radial movement so that when relative rotation (e.g. clockwise) between the housing 10 and the drive member 16 tends to uncoil the clutch spring 20 the clutch spring will first engage the inner wall 13 with the open end 26 rather than at some location between the two ends 24 and 26. This assures that whenever the clutch spring 20 is to be engaged, it will reliably engage the inner wall 13 throughout the length of the clutch spring 20, and stop that relative rotation with a minimum of unpredictable slippage. In this embodiment of the invention, relative rotation in the opposite direction (e.g. counterclockwise) lets the open end 26 of the clutch spring slip by the inner wall 13 of the housing without opposing that relative rotation. In other words, the clutch spring 20 remains in the same coiled position shown in FIG. 2 while rotating within the annular space 18 if the wrench is turned counterclockwise. Accordingly, the coiled spring 20 in the annular space 18 thus functions as a stepless, unidirectional clutch.

Figure 5A:
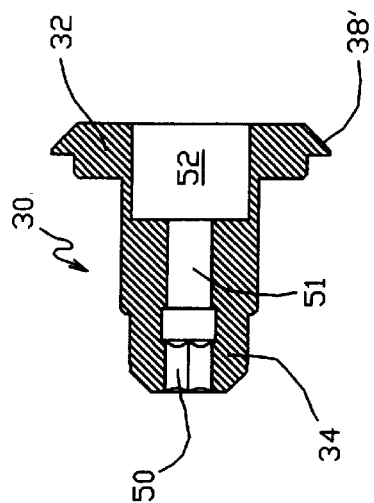
FIGS. 5a and 5b are cross-sectional and end views, respectively, of the rotor body of FIG. 1.
Figure 5B:
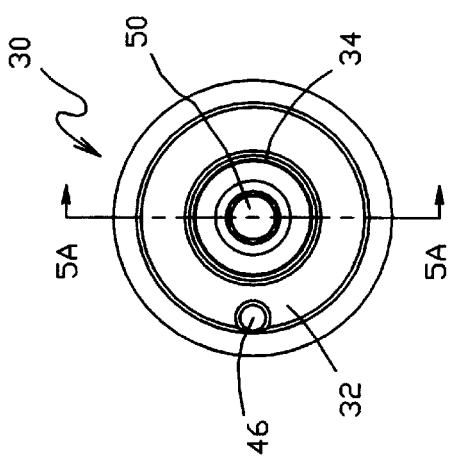
Figure 5C:
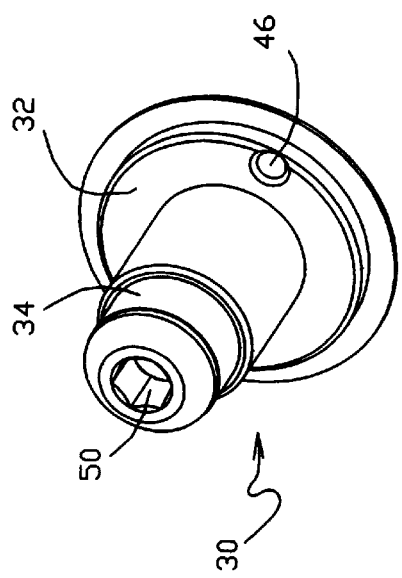
FIG. 5c is an isometric view of the rotor body.
Figure 11D:
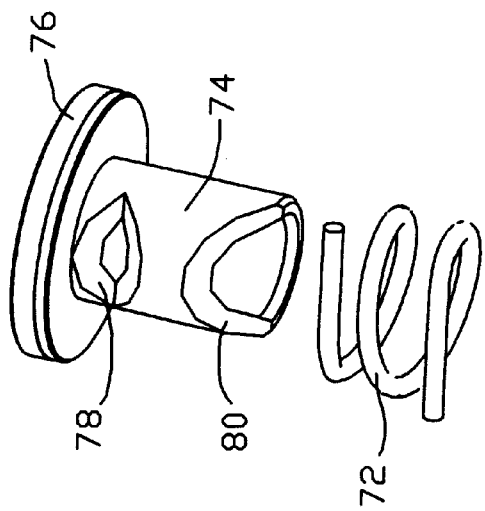
FIGS. 11a–11d show details of the assembled spring and latch body of the tool holder of FIG. 10.
Figure 11B:
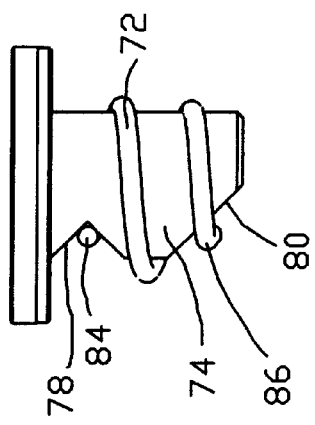
Figure 11C:
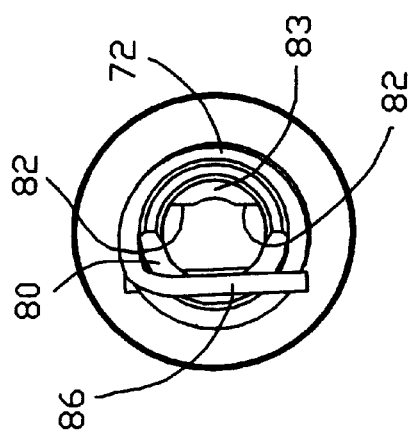
Figure 11A:
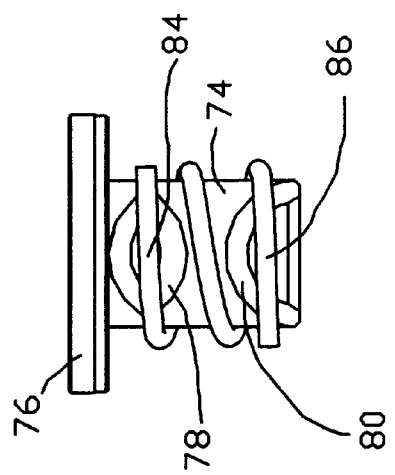

Referring again to FIGS. 1 and 2, and to FIGS. 5a, 5b and 5c, the rotor body 30 is supported within the driver member 16. At one end, the rotor body 30 has a flanged head 32 which rests on and in one end of the driver member 16. At its other end 34, the rotor body 30 has a reduced diameter where the rotor body 30 is supported coaxially in the driver member 16 by two coaxially interfitting hubs 36 and 38 which are shown in detail in FIGS. 6a–6b. The first hub 36 is press-fitted into interlocking engagement with the end of the driver member 16 that is remote from the flanged head 32 and overlies the adjacent ends 11 and 17, respectively, of the housing 10 and the driver member 16. The second hub 38 has a central bore which is press-fitted over the smaller-diameter end 34 of the rotor body 30. The second hub 38 fits rotatably within the first hub 36 and overlies its end surface 37.

A torsion spring 40 has a coiled shape with two ends 42 and 44 extending in opposite directions generally parallel to the axis of rotation of the rotor body 30 as seen best in FIGS. 8a–8c. The upper end 42 fits in a hole 46 in the underside of the flanged head 32 of the rotor body 30, as shown in FIG. 1, and is anchored to the rotor body 30. The bottom end 44 engages in a hole 48 in the body of the first hub 36 and is thereby anchored in the first hub 36 and, through it, to the driver member 16 as seen in FIG. 1. The ends 42 and 44 of this spring 40 need not be collinear, but can be relatively displaced around the axis of the housing 10 as shown in FIG. 8d. If the ends 42 and 44 of the spring 40 are so displaced, the first hub 36 can be correspondingly displaced around the axis to locate the hole 48 to accommodate the location of the end 44 which is engaged in that hole 48. The torsion spring 40 is preferably made of the 303 Series Stainless Steel and has a diameter of about 0.05 inches (1.25 mm).

In use, the housing 10, acting through the clutch spring 20, turns the driver member 16. The driver member 16 and the interlocked first hub 36, when turned, will turn the rotor body 30 through the torsion spring 40 which connects the hub 36 and the rotor body 30. When the rotor body 30 encounters resistance to turning, a force is applied to the torsion spring 40 resulting in the driver member 16, and with it, the first hub 36 being displaced rotationally relative to the rotor body 30 and second hub 38. The magnitude of the displacement angle corresponds to the torque applied to the torsion spring 40.

Marks 39A, 39B and 39C are provided on the surfaces 38' and 36' of the driver member 16 and the rotor body 30 to indicate a precalibrated magnitude of this torque.

When the torque magnitude is zero, the mark 39B on the driver member 16 is adjacent the mark 39A on the rotor body 30. When the rotor body 30 is held against rotation and the driver member rotates around its common axis the second mark 39C on the driver member 16 moves toward the mark 39A on the rotor body 30 and reaches the mark 39A when the precalibrated torque value is reached. Of course, the invention contemplates the use of several markings corresponding to various torque levels. In one embodiment, each wrench is calibrated by the manufacturer to ensure that the torsion spring 40 will produce the torque corresponding to the markings 39A, 39B, and 39C.

Referring again to FIGS. 5a, 5b and 5c, the rotor body 30 is adapted to hold various tools. A socket 50 is provided in the smaller end 34 for the reception of a tool. While the socket 50 has a hexagonal cross-sectional shape, its shape is merely exemplary since other shapes can be used. A cavity 52 in the opposite end of the rotor body 30 opens through the head 32 providing for auxiliary tool holders, examples of which are shown in FIGS. 9 to 15, inclusive.

FIG. 9 shows the pertinent part of a tool 56 comprising a shaft having an "ISO"(International Standards Organization) type dental tool latch which is in general use in dentistry. The latching head 58 has an annular groove 60, an axially-oriented flat surface 62 terminating at a transverse surface 63, which are characteristic of this type of the latching head 58. The tool holders shown in FIGS. 10 to 15, inclusive, are designed to engage tools using the ISO-type latch.

FIGS. 10–11 illustrate one such tool holder 70, employing a spring 72 coiled around a tubular body 74 having a top flange 76 which can be press-fitted into the cavity 52 with the tubular body 74 located within the passage 51 leading to the socket 52. The body 74 has a notch 78 and a bevel 80 formed in one side and a partial shoulder 83 bearing a transverse flat surface 82 on the inner wall opposite the notch 78 and bevel 80. The spring 72 is coiled around the body 74 with its first end 84 terminating in a straight segment resting in the notch 78 and its second end 86 terminating a straight segment resting adjacent to the bevel 80.

Figure 12D:
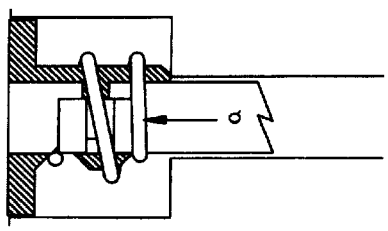
Figure 12I:
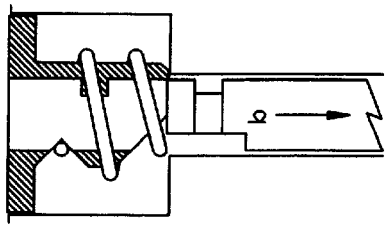
Figure 12C:
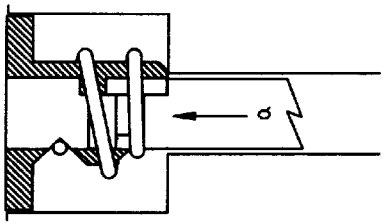
Figure 12H:
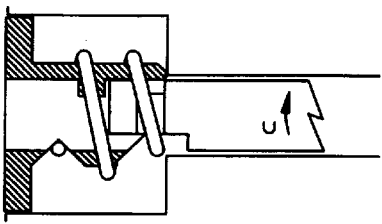
Figure 12B:
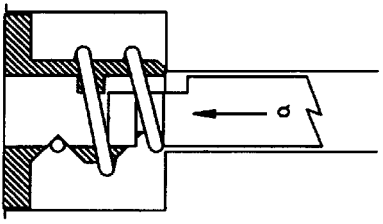
Figure 12G:
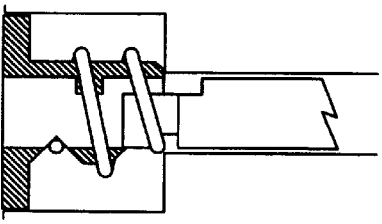
Figure 12A:
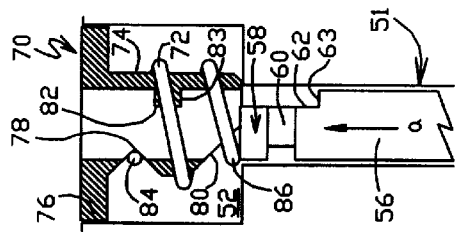
Figure 12F:
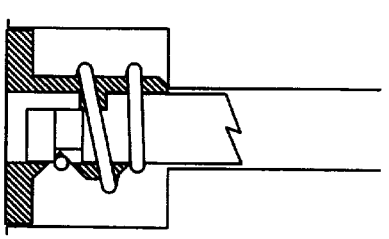
Figure 13D:
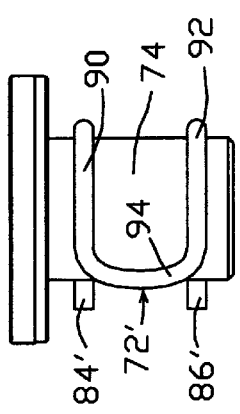
FIGS. 13a–13g show a variation of FIGS. 10 and 11 using a different spring member.
Figure 13G:
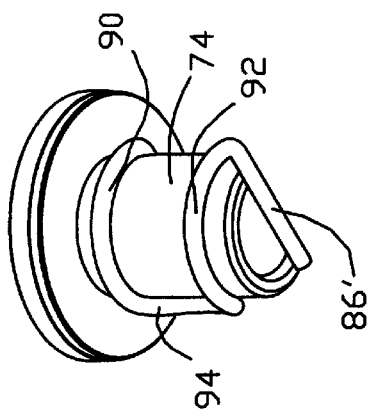
Figure 13C:
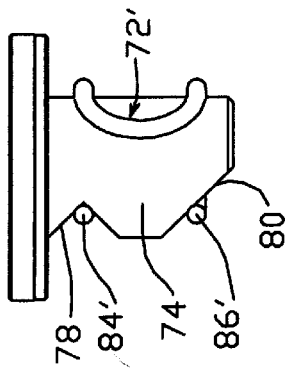
Figure 13F:
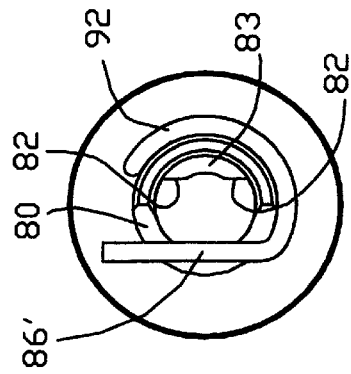
Figure 13B:
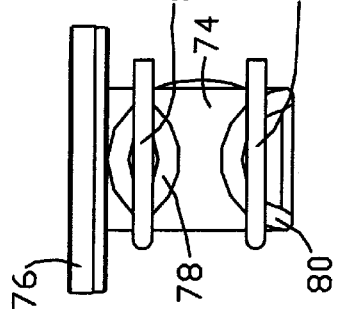
Figure 13E:
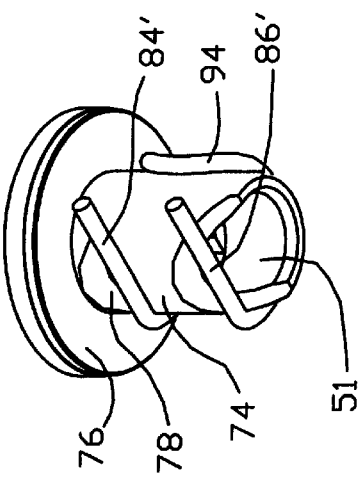
Figure 13A:
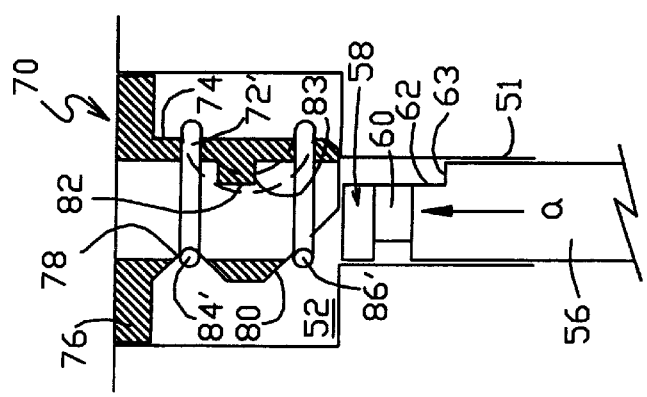

In use as shown in FIG. 12, the latch head 58 of the tool 56 is moved into the tool holder 70 through the socket 50 and the passage 51 leading to the cavity 52 with its flat surface 62 oriented to move past the flat surface 82 of the partial shoulder 83 as indicated by the vertical arrow "a" in FIG. 12a. Eventually, the head 58 encounters the second end 86 of the spring 72 at which point further movement into the tool holder 70 pushes the coil at the second end 86 of the spring 70 upward to an approximately horizontal position as shown in FIG. 12b. At this point, the head 58 can move past that coil into the body 74 as shown in FIG. 12c. Now the lower coil at the second end 86 rests in the annular groove 60 of the latch head 58. The latch can be moved further into the body 74 with the flat surface 62 passing by the flat surface 82 of the partial shoulder 83 as shown in FIG. 12*d*. Moving the latch further into the body 74, the head 58 encounters the first end 84 of the spring 72 and pushes it slightly out of the notch 78 as shown in FIG. 12*e*. Finally, as is shown in FIG. 12*f*, the latch head 58 comes to rest firmly latched in the tool holder 70 with the first end 84 of the spring 72 engaged in the annular groove 60 and the flat surface 62 of the latch engaged against the flat surface 82 of the partial shoulder 83. Additionally, the transverse surface 63 of the latch head 58 is engaged against the underside of the partial shoulder 83 and the coil 86 at the second end of the spring embraces the shaft of the tool 56 beneath the annular groove 60.

When the tool 56 is installed in the tool holder 70, the latter being installed in the cavity 52, the shaft passes through the passage 51 and the socket 50 in the rotor body 30. Thus, all tools installed in the rotor body 30 will extend in the same direction from the wrench and the torque-indicator marks 39A, 39B and 39C will at all times be visible when the wrench is in use.

Removing the tool 56 from the tool holder 70 is illustrated in FIGS. 12*g* to 12*j*. A pull-out force indicated by an arrow "b" in FIG. 12*g* forces the first end 84 of the spring 72 out of the notch 78 and moves the flat surface 62 by the surface 82 of the partial shoulder 83. The latch is then disengaged from the shoulder 83 and the annular groove 60 is held by the coil at the second end 86 of the spring as shown in FIG. 12*h*. At this point the tool 56 is turned 180° as is indicated by an arrow "c" in FIG. 12*i*, presenting the flat surface 62 to the second end 86 of the spring. The tool 56 is now free to be removed from the tool holder 70 as seen in FIG. 12*j*.

FIGS. 13*a–g*, inclusive, show a tool holder similar to the one shown in FIGS. 10 and 11 employing a spring 72' differing in form from the spring 72 but performing the same functions. The spring 72' has straight segments 84' and 86' deployed in the notch 78 and adjacent the bevel 80, respectively, like the straight spring segments at the ends 84 and 86 in FIGS. 10–11. However, rather than being at the ends of the coil spring 72, the straight segments 84' and 86' in FIG. 14 are each part of a D-shaped part 90 or 92, respectively, enveloping the tubular body 74. These D-shaped parts 90 and 92 are joined together by a bight segment 94.

Figure 15:
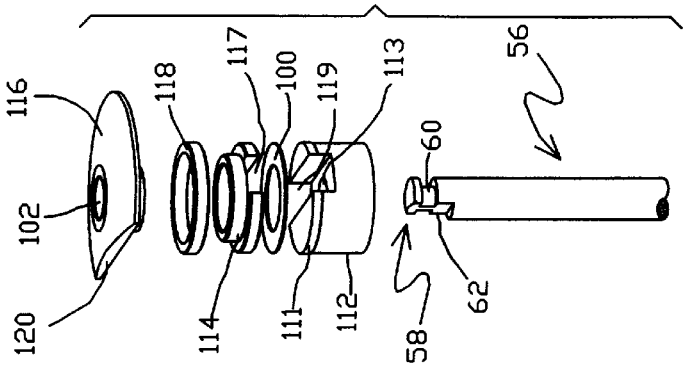
FIG. 15 is an exploded view of FIG. 14.

Another alternative tool holder 110, shown in FIGS. 14 and 15, comprises a main body 112, a latch body 114, a latch handle 116, a spacer washer 118 and a shim 100. In use, all components except the latch handle 116 are installed in the cavity 52 in the rotor body 30. The latch handle 116 overlies the rotor body 30 (not shown).

The main body 112 and the spacer washer 118 are press-fitted into the cavity 52 which is aided by the expanded land region 111 on the main body 112. The latch body 114 and the latch handle 116 are press-fitted together. The latch body 114 has an opening 117 which can be brought into register with a cross passage 119 in the main body 112 under control of the latch handle 116. The latch body 114 has also a dog 115 opposite the entrance into the opening 117. The tool 56 is insertable into the tool holder 110 through a passage 113 in the main body 112 which communicates with the cross passage 119 to place the latch head 58 in an opening 102 in the latch handle 116.

Figure 14B:
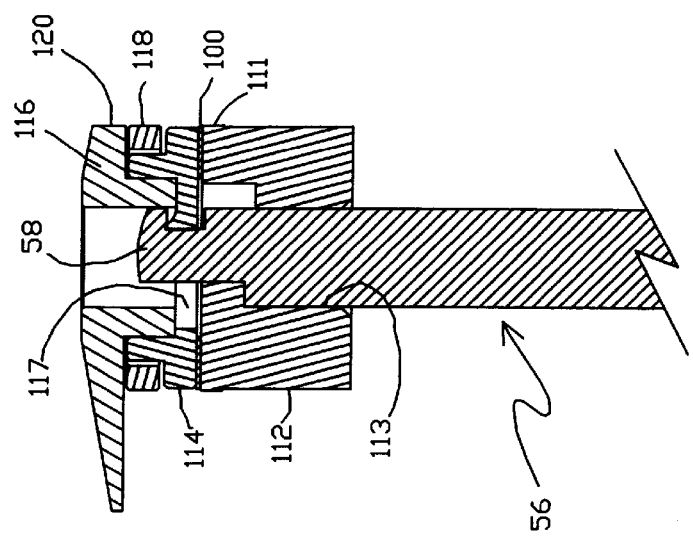
FIGS. 14a and 14b are sectional views of another ISO-type tool latch.
Figure 14A:
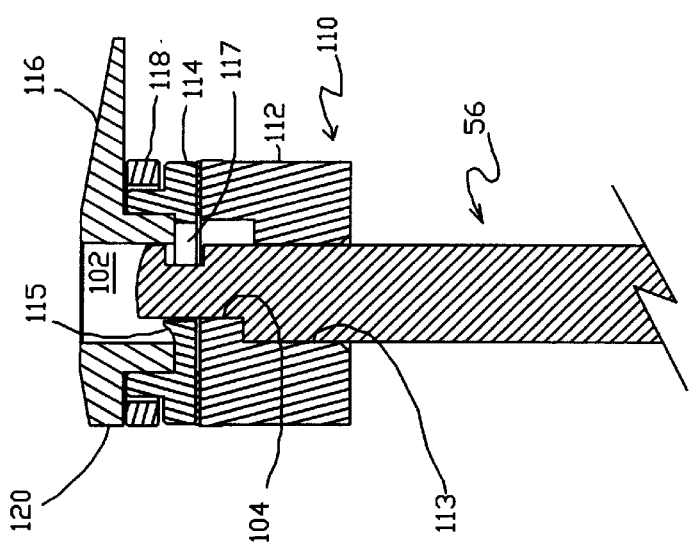

As is shown in FIG. 14*a*, the main body 112 has a partial shoulder 104 extending into the passage 113 which engages the flat side 62 of the tool 56 and thereby guides the tool 56 to be inserted with a prescribed orientation around its longitudinal axis to allow the latch head 58 to enter the opening 102 in the latch handle 116. After the tool 56 is correctly inserted into the tool holder 110, the latch handle 116 is rotated approximately 180° to place the dog 115 in the groove 60 of the tool and thereby lock the tool 56 in place in the tool holder 110, as is illustrated in FIG. 14*b*. A flat surface 120 across the latch handle 116 is useful to turn the latch handle 116 and to indicate the locked position.

The torque indicator wrench that is described herein is a one-way wrench, useful to apply torque to a screw or a bolt in one direction but not the opposite direction. It is intended for use to tighten a screw to a prescribed torque, as is desired in implant dentistry, by allowing the clinician to visualize the relative position of the marking 39A to the other torque markings 39B and 39C. Moreover, a ratchet wrench of the present invention can be made quite small. The housing 10 may have a diameter of about 0.75 inch or less and the height of housing 10, with the hubs and rotor body attached, is about 0.5 inch or less.

Because there is typically no need to be concerned with torque levels when removing a screw, the dental practitioner can use an ordinary tool for that task. Thus, the torque-indicator wrench of the present invention can be designed for the one task where it is needed, thereby providing the needed wrench at minimum cost to the practitioner. However, a bidirectional wrench can be provided by adding a similar tool socket, like the socket 50, at both ends of the passage 51 in the rotor body 30. For that purpose, torque-indicator marks would be useful on both axial ends of the wrench. The clinician desiring to reduce the torque on a screw to a known amount could do so by turning the wrench over and using the opposing socket.

Figure 17:
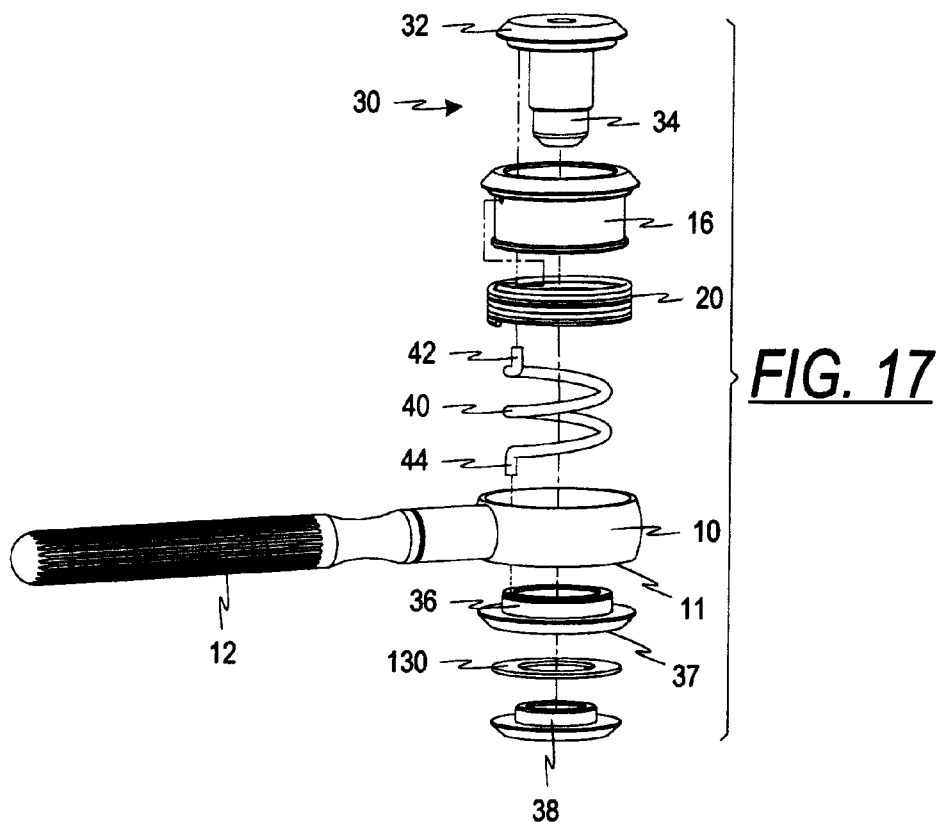
FIG. 17 is an exploded view of FIG. 16.
Figure 16:
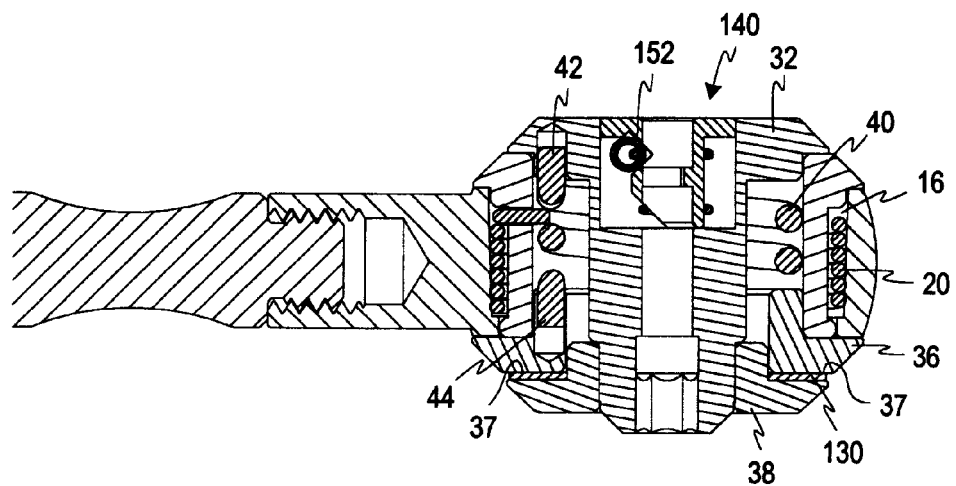
FIG. 16 is a longitudinal sectional view of the wrench including a friction educing washer.
Figure 18E:
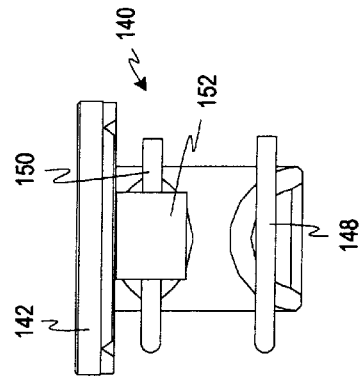
FIGS. 18a–18f are various views of an alternative ISO-type latch body.
Figure 18D:
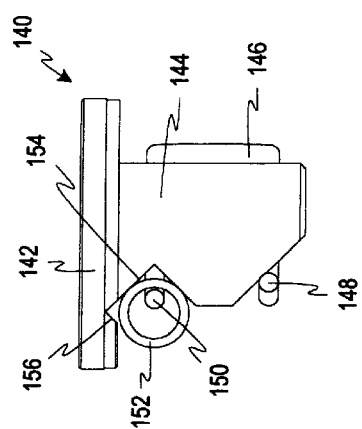
Figure 18F:
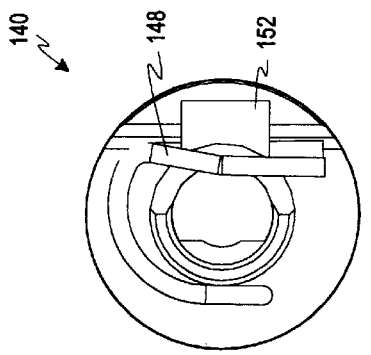
Figure 18C:
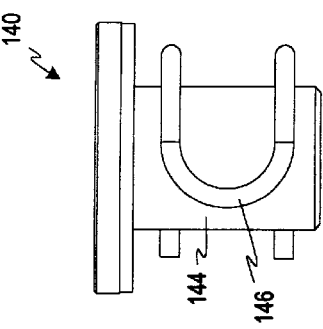
Figure 18B:
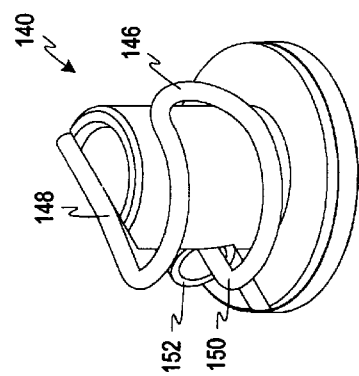
Figure 18A:
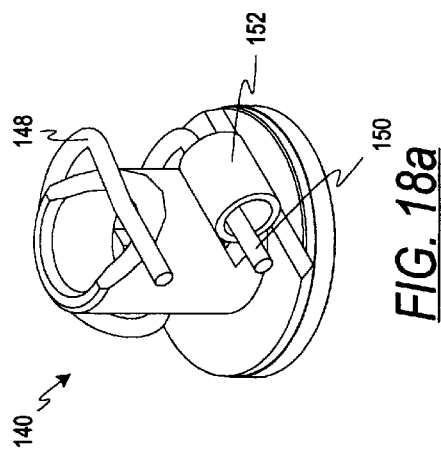

FIGS. 16–17 illustrates an alternative torque indicator ratchet wrench similar to the one described above, but which includes a washer 130 between the first hub 36 and the second hub 38 to provide smoother movement to the wrench. The washer 130 is preferably made of a lubricious material to reduce the friction between the first and second hubs 36, 38. Further, the material should be able to withstand the environment of an autoclave and also be relatively rigid so as avoid distortion when operational forces are applied thereto. One example of a material that provides these desired qualities is Teflon®. An example of a metallic material is a metal with a gold coating where the gold coating acts as a lubricant.

By reducing the friction between the first and second hubs 36, 38, the washer 130 provides a smoother feel during ratcheting. While not affecting the accuracy of the torque indicating feature, the washer 130 enhances the ability of the marking 39A on the rotor body 30 to return to the zero-torque marking 39B on the drive member 16. As mentioned above, each wrench is individually calibrated to ensure the markings 39A, 39B, and 39C are properly placed. Thus, these markings 39A, 39B, 39C are typically placed on the wrench after it has been fully assembled and calibrated. However, the washer 130 provides much more uniformity from the wrench to wrench such that, when the torsion springs 40 are uniform in their spring force, it has become relatively feasible to provide the markings before final assembly.

Further, to reduce the other frictional forces present in the wrench, a washer like washer 130 may be placed the rotor body 30 and the driver member 16. Further, a cylindrical friction-reducing member (e.g. a Teflon® cylinder) may be placed on the walls of the driver member 16 to reduce the frictional engagement with the spring 40. This further enhances uniformity for wrench to wrench.

FIG. 18 shows a latching tool holder 140 that is similar to the tool holder in FIGS. 13a–13g. The tool holder 140 includes a top flange 142 and a tubular body 144. The holder 140 is press fit into cavity of the wrench as shown in FIG. 16 and generally described above with reference to FIGS. 10–13. The spring 146 has a lower tool-engaging portion 148 and an upper tool-engaging portion 150. The upper tool-engaging portion 148 is placed within a cylindrical roller 152 that is resident within a notch 154 in the tubular body 144, unlike the previous configurations where the tool-engaging portion of the spring directly engages the notch.

The cylindrical roller 152 has a diameter that is small enough to protrude past the inner wall of the tubular body 144 such that it will encounter the annular groove 60 on the head 58 of the tool (as shown in FIG. 9 by itself, and FIG. 12 in operation). The cylindrical roller 152 preferably has a diameter that is at least slightly larger than the axial dimension of the annular groove 60 and protrudes past the inner wall of the tubular body 144 by a small amount, usually less than 0.025 inch. The top flange 142 may also include a relief cut-out 156 to allow the cylindrical roller 152 to seat properly within the notch 154.

Unlike the configuration of FIGS. 12 and 13 where the movement of the tool-engaging portion of the spring into and out of the annular groove 60 may be difficult due to the head 58 above the groove 58 and the shoulder below the groove 58, the cylindrical roller 152 smoothly rolls into and out of the groove 60. Accordingly, the clinician is much less likely to encounter any problems during the insertion or removal of the tool from the tool holder 140.

In another variation to the cylindrical detent ISO-latch mechanism of FIGS. 18, the tool holder 140 can lack the notch 154 and the spring 146. Instead, the lower end of the tool holder 140 opposite the top flange 142 has a plurality of resilient fingers that project slightly inwardly into the cylindrical cavity formed by the tool holder 140. The tool, when inserted into the tool holder 140, forces the resilient fingers radially outward and is snugly held by the fingers. The tool is then rotated as in the previous embodiments so at to have its flat surface engage the corresponding flat surface on the shoulder within the tool holder 140. Utilizing the resilient fingers has the benefit of retaining the tool at nearly every position during the insertion and removal processes. Further, it is less costly since it does not need the spring or special machining cuts in the cylindrical surface of the tool holder. Also, it is possible to make this type of tool holder by having a separate part containing the resilient fingers press-fitted into the opening at the lower end of the tool holder. Additionally, the internal shoulder having the flat that engages the flat of the tool could be formed by inserting another separate part having the D-shaped interior into the opening at the flange end of the tool holder.

While the present invention has been described with reference to one or more preferred embodiments, those skilled in the art will recognize that many changes may be made thereto without departing from the spirit and scope of the present invention which is set forth in the following claims.

What is claimed is:

1. A dental ratchet wrench for applying torque to a fastener that is used in a dental prosthesis, comprising:
    a housing;
    a drive member located within said housing;
    a slip clutch spring coupled to said housing and said drive member, said slip clutch spring causing said drive member to rotate with said housing when said housing is rotated in one direction, said slip clutch spring causing said drive member to rotate relative to said housing when said housing is rotated in the opposite direction; a rotor coupled to said drive member via a straight coil torsion spring, said rotor including means for receiving a tool for rotating said fastener; and
    torque indicators on at least one said drive member and said rotor at known angular positions corresponding to predetermined torque values, said torque indicators progressively illustrating the amount of torque being exerted by said rotor.

2. The dental ratchet wrench of claim 1, wherein said housing and said driving member define a region having an annularly shaped cross-section, said annularly shaped cross-section having a narrower portion.

3. The dental ratchet wrench of claim 2, wherein said narrower portion is dimensioned to catch a free end of said slip clutch spring when said housing is rotated in said one direction, while allowing said free end to rotate with respect to said housing when said housing is rotated in said other direction.

4. The dental ratchet wrench of claim 1, wherein said torsion spring has two free ends that extend in the axial direction with respect to said housing.

5. The dental ratchet wrench of claim 1, wherein said rotor includes a lower hub, said torsion spring being connected to said lower hub and passing internally through said drive member to an upper flange of said rotor, said torsion spring being connected to said upper flange.

6. The dental ratchet wrench of claim 1, wherein said rotor and said drive member have complementary confronting surfaces that rotate relative to each other, said dental ratchet wrench further including a lubricating region between said confronting surfaces for reducing friction.

7. The dental ratchet wrench of claim 6, wherein said rotor and said drive member each have lower hubs, said complementary confronting surfaces being located on said lower hubs.

8. The dental ratchet wrench of claim 7, wherein said lubricating region is a washer is made of Teflon.

9. The dental ratchet wrench of claim 8, wherein said torque indicators are placed on said dental ratchet wrench before final assembly.

10. The dental ratchet wrench of claim 1, wherein said receiving means includes at least two different regions for receiving two types of tools.

11. The dental ratchet wrench of claim 10, wherein a first region includes a polygonal socket and a second region includes an ISO-type tool holder.

12. The dental ratchet wrench of claim 11, wherein said second region is accessible by an ISO-type tool by extending said ISO-type tool through said first region.

13. A dental ratchet wrench for applying a known amount of torque to a fastener that is used in a dental prosthesis, comprising:
    a housing;
    a drive member located primarily within said housing, said housing and said drive member defining a first region therebetween;

a tool receiving component for receiving a tool to exert torque on said fastener, said tool receiving component located primarily within said drive member, said tool receiving component and said drive member defining a second region;

a torsion spring located within said second region, said torsion spring having one end connected to said drive member and the other end connected to said tool receiving component, a certain angular displacement of said one end relative to said other end producing a certain torque on said tool receiving component;

a slip clutch located within said first region, said slip clutch causing said drive member to rotate with said housing when said housing is rotated in one direction, said slip clutch causing said drive member to rotate relative to said housing when said housing is rotated in the opposite direction; and torque indicators on at least one of said drive member and tool receiving component corresponding to predetermined torque values, said torque indicators progressively illustrating the amount of torque being exerted by said tool receiving component.

14. The dental ratchet wrench of claim 13, wherein said first region has an annularly shaped cross-section, said annularly shaped cross-section having a narrower portion.

15. The dental ratchet wrench of claim 14, wherein said slip clutch is a spring and said narrower portion is dimensioned to catch a free end of said spring when said housing is rotated in said one direction, while allowing said free end to rotate with respect to said housing when said housing is rotated in said other direction.

16. The dental ratchet wrench of claim 13, wherein said tool receiving portion includes a lower hub and said drive member has an upper flange, said lower hub and said upper flange at least partially defining said second region, said one end of said torsion spring being connected to said lower hub and said other end of said torsion spring being connected to said upper flange of said rotor.

17. The dental ratchet wrench of claim 13, wherein said tool receiving portion and said drive member have complementary confronting surfaces that rotate relative to each other, said complementary confronting surfaces including a lubricating region for reducing friction.

18. The dental ratchet wrench of claim 17, wherein said lubricating region includes a washer that is made of Teflon.

19. The dental ratchet wrench of claim 13, wherein said tool receiving portion has two distinct portions for receiving two distinct tools.

20. The dental ratchet wrench of claim 19, wherein a first portion includes a polygonal socket and a second portion includes an ISO-type tool holder.

21. The dental ratchet wrench of claim 13, wherein said torsion spring has two free ends that extend in the axial direction.

22. The dental ratchet wrench of claim 13, wherein said tool receiving portion includes an ISO-type tool holder.

23. The dental ratchet wrench of claim 22, wherein said ISO-type tool holder includes a cylindrical body having a plurality of cut-outs and a spring for wrapping around said body, portions of said spring extending within said cut-outs.

24. The dental ratchet wrench of claim 23, wherein said spring has a D-shape.

25. The dental ratchet wrench of claim 23, wherein said spring is a coil spring.

26. The dental ratchet wrench of claim 22, wherein said ISO-type tool holder includes a rotatable latch for locking the tool in place.

27. The dental ratchet wrench of claim 22, wherein said ISO-type tool holder includes a cylindrical detent within one of said cut-outs.

28. The dental ratchet wrench of claim 13, wherein a diameter of said housing is less than about 0.75 inch.

29. The dental ratchet wrench of claim 13, wherein said torsion spring is made of a stainless steel.

30. The dental ratchet wrench of claim 29, wherein said torsion spring is made of stainless steel wire stock having a diameter of about 1.25 mm.

31. The dental ratchet wrench of claim 13, wherein said torque indicators includes a plurality of torque-number markings on said drive member and one marking on said tool receiving component, said one marking on said tool receiving component moving relative to said plurality of torque-number markings while said torque is being exerted.

32. The dental ratchet wrench of claim 13, wherein said tool receiving component has upper and lower tool receiving portions allowing said wrench to be used to reverse the torque on said screw.

33. A dental wrench for applying torque to a fastener used in a dental prosthesis, comprising:

a housing;

a drive member located primarily within said housing;

a tool receiving component coupled to and located adjacent to said drive member, said tool receiving component for receiving a tool to exert torque on said fastener, said tool receiving component including an ISO-type tool holder for holding a dental tool having an ISO-type latch; and torque markings representing corresponding torque values on at least one of said drive member and said tool receiving component.

34. The dental ratchet wrench of claim 33, wherein said ISO-type tool holder includes a cylindrical body having a plurality of cut-outs and a spring for wrapping around said body, portions of said spring extending within said cut-outs.

35. The dental ratchet wrench of claim 34, wherein said spring has a D-shape.

36. The dental ratchet wrench of claim 34, wherein said spring is a coil spring.

37. The dental ratchet wrench of claim 33, wherein said ISO-type tool holder includes a rotatable latch for locking the tool in place.

38. The dental ratchet wrench of claim 33, wherein said ISO-type tool holder includes a cylindrical detent within one of said cut-outs.

39. A ratchet wrench for applying torque to a fastener, comprising:

a drive member;

a rotor coupled to and located adjacent to said drive member, said rotor for exerting said torque on said fastener;

a ratcheting mechanism allowing said drive member to move said rotor in one direction; and a plurality of torque markings representing corresponding torque values on at least one of said drive member and said rotor, said torque markings progressively illustrating the torque that said rotor places on said fastener.

40. The ratchet wrench of claim 39, wherein said plurality of torque markings includes a plurality of torque-number markings on said drive member and a single marking on said tool receiving component, said single marking on said rotor moving relative to said plurality of torque-number markings while said torque is being exerted.

41. The ratchet wrench of claim 39, wherein said rotor and said drive member are coupled through a straight coil torsion spring located between said rotor and said drive member.

* * * * *

UNITED STATES PATENT AND TRADEMARK OFFICE
CERTIFICATE OF CORRECTION

PATENT NO. : 6,186,785 B1
DATED : February 13, 2001
INVENTOR(S) : Rogers et al.

It is certified that error appears in the above-identified patent and that said Letters Patent is hereby corrected as shown below:

Title page,
Item [56], OTHER PUBLICATIONS, delete "Torqus" and insert -- Torques -- and delete "Surgica" and insert -- Surgical --

Column 6,
Line 59, after "from" delete "the"

Column 8, claim 1,
Line 12, after "direction" insert paragraph

Column 8, claim 8,
Line 48, after "washer" delete "is"

Column 10, claim 31,
Line 9, delete "indicators" and insert -- indicator --

Column 10, claim 40,
Line 58, delete "includes" and insert -- include --
Line 60, delete "tool receiving component" and insert -- rotor --

Signed and Sealed this

Ninth Day of April, 2002

Attest:

JAMES E. ROGAN
Attesting Officer
Director of the United States Patent and Trademark Office